(12) United States Patent
Rabbitte et al.

(10) Patent No.: US 8,118,830 B2
(45) Date of Patent: Feb. 21, 2012

(54) METHOD FOR REDUCING EMBOLI FORMATION

(75) Inventors: Gerard Rabbitte, Tuam (IE); Ronald Kelly, Oranmore (IE)

(73) Assignee: Salviac Limited, Dublin (IE)

( * ) Notice: Subject to any disclaimer, the term of this patent is extended or adjusted under 35 U.S.C. 154(b) by 73 days.

(21) Appl. No.: 12/211,271

(22) Filed: Sep. 16, 2008

(65) Prior Publication Data
US 2010/0069950 A1    Mar. 18, 2010

(51) Int. Cl.
*A61M 29/00* (2006.01)

(52) U.S. Cl. ....................... 606/200; 623/903

(58) Field of Classification Search .......... 606/200, 606/191–194, 108, 110, 113, 127, 159, 198; 604/19, 22, 35, 46; 623/1.11, 1.12, 903
See application file for complete search history.

(56) References Cited

U.S. PATENT DOCUMENTS

| | | | |
|---|---|---|---|
| 4,723,549 A | 2/1988 | Wholey et al. | |
| 5,053,008 A | 10/1991 | Bajaj | |
| 5,108,419 A | 4/1992 | Reger et al. | |
| 5,728,068 A * | 3/1998 | Leone et al. | 604/101.01 |
| 5,807,330 A | 9/1998 | Teitelbaum | |
| 6,336,934 B1 | 1/2002 | Gilson et al. | |
| 6,485,500 B1 * | 11/2002 | Kokish et al. | 606/194 |
| 6,544,279 B1 * | 4/2003 | Hopkins et al. | 606/200 |
| 6,551,342 B1 | 4/2003 | Shen et al. | |
| 6,830,579 B2 * | 12/2004 | Barbut | 606/200 |
| 6,923,822 B2 * | 8/2005 | Crawford et al. | 606/194 |
| 6,986,778 B2 * | 1/2006 | Zadno-Azizi | 606/200 |
| 7,094,249 B1 * | 8/2006 | Broome et al. | 606/200 |
| 2003/0014071 A1 | 1/2003 | Reynolds et al. | |
| 2003/0065354 A1 | 4/2003 | Boyle et al. | |
| 2004/0260332 A1 * | 12/2004 | Dubrul et al. | 606/200 |
| 2006/0259066 A1 * | 11/2006 | Euteneuer | 606/200 |
| 2007/0021685 A1 | 1/2007 | Oepen et al. | |

* cited by examiner

*Primary Examiner* — Elizabeth Houston
(74) *Attorney, Agent, or Firm* — Sughrue Mion, PLLC; Jonathan Feuchtwang

(57) ABSTRACT

Methods and devices for reducing emboli formation during medical procedures. In accordance with the present invention a first medical device is passed through a stenosed area and activated to block fluid flow through the lumen, a second medical device including a filter is passed through the stenosed area and deployed. The first medical device is then deactivated to restore fluid flow through the lumen.

19 Claims, 5 Drawing Sheets

METHOD FOR REDUCING EMBOLI FORMATION

FIELD OF THE INVENTION

The present invention relates generally to medical procedures, and, more particularly, to methods for reducing emboli formation.

BACKGROUND OF THE INVENTION

The term "STROKE" is used to describe a medical event whereby blood supply to the brain or specific areas of the brain is restricted or blocked to the extent that the supply is inadequate to provide the required flow of oxygenated blood to maintain function. The brain will be impaired either temporarily or permanently, with the patient experiencing a loss of function such as sight, speech or control of limbs. There are two distinct types of stroke, hemorrhagic and embolic. Embolic stroke may be caused by embolic material that may become dislodged after stenting.

Medical literature describes artery disease as a significant source of embolic material. Typically, an atherosclerotic plaque builds up in the arteries. The nature of the plaque varies considerably, but in a significant number of cases pieces of the plaque can break away and flow distally and, for example, block blood flow to specific areas of the brain and cause neurological impairment, plaque can also break free and flow into the lungs or heart and cause other adverse events. Treatment of the disease in the carotid artery is classically by way of surgical carotid endarterectomy whereby, the carotid artery is cut and the plaque is physically removed from the vessel. The procedure has broad acceptance with neurological complication rates quoted as being low, somewhere in the order of 5% although claims vary widely on this.

Not all patients are candidates for surgery. A number of reasons may exist such that the patients could not tolerate surgical intervention. In these cases and in an increasing number of candidates that are surgical candidates are being treated using transcatheter techniques. In this case, the evolving approach uses devices inserted in the femoral artery and manipulated to the site of the stenosis. A balloon angioplasty catheter is inflated to open the artery and an intravascular stent is sometimes deployed at the site of the stenosis. The action of these devices as with surgery can dislodge embolic material which will flow with the arterial blood and if large enough, eventually block a blood vessel and cause a stroke.

It is known to permanently implant a filter in human vasculature, such as the vena cava, to catch embolic material. It is also known to use a removable filter for this purpose. Such removable filters typically comprise umbrella type filters comprising a filter membrane supported on a collapsible frame on a guidewire for movement of the filter membrane between a collapsed position against the guidewire and a laterally extending position occluding a vessel. Examples of such filters are shown in U.S. Pat. No. 4,723,549, U.S. Pat. No. 5,053,008, and U.S. Pat. No. 5,108,419. Various deployment and/or collapsing arrangements are provided for the umbrella filter.

Improved filter devices such as those shown in U.S. Pat. No. 6,336,934 and U.S. Pat. No. 6,551,342 and US Patent Application Publication No. 2003/0065354, the entireties of which are hereby incorporated by reference, have been designed to overcome the shortcomings of the previous filters. For example, in one embodiment, the filter is freely disposed along the length to the guidewire, thereby allowing the guidewire to be moved independently of the filter assembly. U.S. Pat. No. 6,336,934 discloses in one embodiment an embolic protection filter having a collapsed state and an expanded state, the filter having a polymeric filter membrane, a support structure supporting the membrane in the expanded state and a tubular element connected to the support structure and having an aperture for disposing the filter over a delivery device, wherein the filter has a proximal inlet opening and a plurality of distal outlet openings, the outlet openings configured to allow fluid to flow through the filter but retain embolic material within the filter and the inlet opening is larger than any of the outlet openings.

After the filter has crossed the stenosed region of the vessel, the filter is deployed within the vessel to capture any emboli that may be dislodged during subsequent medical procedure(s). However, one problem associated with current embolic protection filter devices is that they must cross the stenosed area(s) before they can be deployed. In some instances the stenosed area may have a restricted diameter such that the filter may drag or knock loose some of the plaque during crossing, thereby causing emboli to be released within the lumen. The emboli may cause complications such as stroke or possibly death.

Therefore, there is a need for an improved embolic protection device, wherein the improved device reduces the risk of emboli formation while crossing a stenosed portion of the lumen.

BRIEF SUMMARY

It is to be understood that both the foregoing general description and the following detailed description are exemplary and are intended to provide further explanation of the invention claimed.

In accordance with the present invention there is provided a method for reducing emboli formation, the method comprising the steps of (1) providing a first medical device having an occlusion member associated with a distal end thereof; (2) advancing the first medical device through an area of a lumen to be treated; (3) activating the occlusion member of the first medical device to restrict fluid flow within the lumen; (4) providing an second medical device including a filter member; (5) passing the second medical device through the area to be treated, and deploying the filter member from a collapsed state to an expanded state, wherein in its expanded state the filter member opposes the lumen; and (6) deactivating the occlusion member of the first medical device.

The accompanying Figures, which are incorporated in and constitute part of this specification, are included to illustrate and provide a further understanding of the method and system of the invention. Together with the description, the Figures serve to explain the principles of the invention.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

Figure 1:
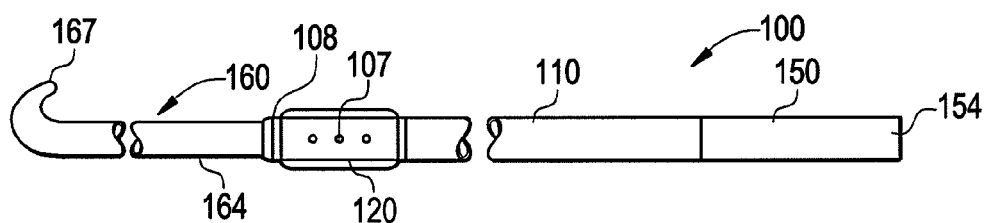
FIG. 1 is a plan view of a temporary embolic protection catheter to be utilized in accordance with the methods of the present invention.

It should be noted that the figures are not drawn to scale and that elements of similar structures or functions are generally represented by like reference numerals for illustrative purposes throughout the figures. It also should be noted that the figures are only intended to facilitate the description of embodiments of the present invention.

DETAILED DESCRIPTION

In accordance with the present invention herein, there is provided devices and methods for embolic protection, more specifically methods and devices for reducing the potential for emboli formation during advancement and deployment of an embolic protection device.

In accordance with the present invention there is provided systems and methods for reducing emboli formation during medical procedures. The embolic system in accordance with the present invention includes an elongated guidewire member, wherein the elongated guidewire member includes an expandable member disposed adjacent to a distal end thereof and a valve assembly disposed at a proximal end thereof. The guidewire is sized to receive an expandable embolic protection filter member, wherein the filter member is translatable and rotatable about the guidewire. The filter member further includes a delivery/retrieval catheter, wherein the filter member is receivable within a space at the distal end of the delivery/retrieval catheter. Each of these components will be described in greater detail below with regard to the appropriate figures.

Figure 2:
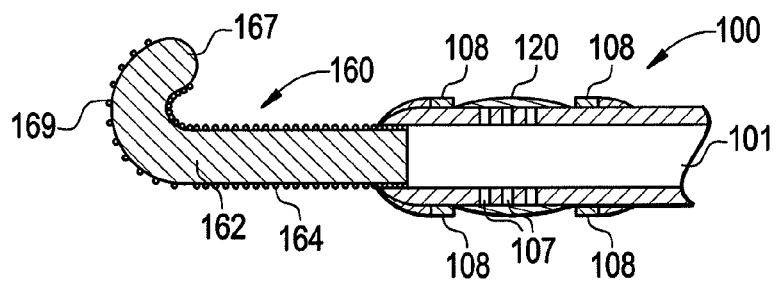
FIG. 2 is an enlarged view of the distal end portion of the catheter of FIG. 1.

Referring now to FIGS. 1 and 2, there is shown an exemplary embodiment of the guidewire 100 in accordance with the present invention. As shown in FIG. 1, there is shown a representative embodiment of a guidewire 100 according to the present invention. The guidewire 100 includes an elongated body 110 having a proximal end portion 154 and a distal end portion 167 and at least one lumen 101 disposed therethrough defining an inner cavity. An inflatable balloon 120 is disposed proximate the distal end portion 167, wherein the inner cavity of the balloon 120 is in fluid communication with the lumen 101 of the guidewire 100.

If desired, at least one radiopaque marker 108 may be disposed at the distal end portion of the elongated body 110 proximate the balloon 120. Preferably, at least one radiopaque marker 108 is disposed within the distal end of the cavity defined by the balloon, and if desired, at least one proximal radiopaque marker 108 is disposed within the proximal end of the cavity defined by the balloon 120. The guidewire 100 also may include a flexible tip 160. The flexible tip 160 may extend from the distal end portion of the guidewire 100.

Figure 3:
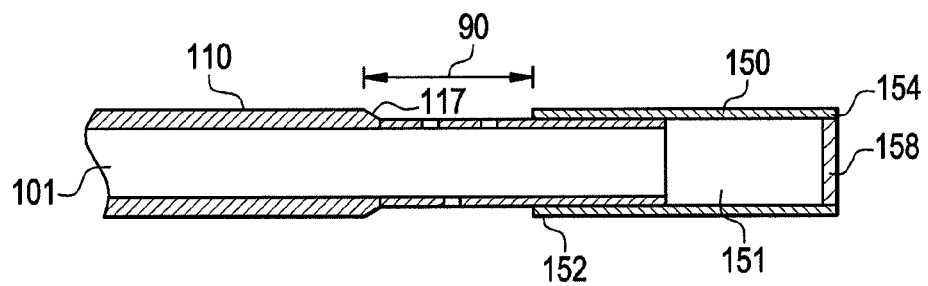
FIG. 3 is a partial cross-sectional view of the proximal end of the catheter of FIG. 1 illustrating a valve assembly in an open configuration.
Figure 4:
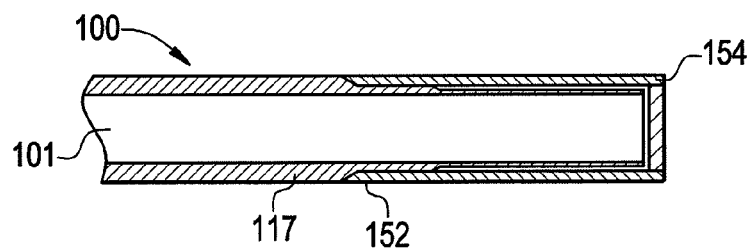
FIG. 4 is a second partial cross-sectional view of an alternative valve assembly shown in a closed embodiment.

Referring now to FIGS. 3 and 4, in accordance with the present invention, the guidewire 100 includes at its proximal end portion 154 a valve body 150, wherein the valve body 150 is movable between a closed position and an open position; the valve body 150 is configured to engage a surface of the elongated body 110 to seal the opening when the valve body 150 is in the closed position. The guidewire 100 will be described in greater detail below.

The elongated body 110 of the guidewire 100 may be constructed of any suitable material including but not limited to polymide material, alloy materials, and metallic materials such as stainless steel hypodermic tubing which is available from MicroGroup® Inc., Medway, Md. Preferably the elongated body 110 of the guidewire 100 is constructed of a nickel titanium alloy known as Nitinol. Materials such as these are available from various suppliers such as Memry Corp., Menlo Park, Calif., U.S. The above materials should not be considered limiting in any manner, it is contemplated that the elongated body 110 may be constructed of any bio-compatible material. For example, the elongated body may be constructed of a polymer such as polymide tubing from Accellent of Trenton, Ga., U.S. The elongated body 110 may be manufactured using well-known techniques such as swaging, machining, grinding, electropolishing, EDM, heat forming, extruding, or by any other processes commonly used to shape and configure small metal or polymer components. Additionally, the elongated body 110 may be constructed from polypropylene or urethane by an extrusion process using an extruder such as that available from Medical Extrusion Technologies, Inc., Murieta, Calif., U.S.

The elongated body 110 may be further coated with any of a variety of materials to enhance performance if desired. For example possible coating materials include lubricious materials such as Teflon™ available from DuPont De Nemours, Wilmington, Del., U.S., and hydrophobic materials such as silicone lubricant dispersion PN 4097, available from Applied Silicone Corp., Ventura, Calif., U.S., or a hydrophilic material such as hydrogel available from Hydromer, Branchburg, N.J., U.S., or lubricious coatings such as those available from Hydro-Silk of Merritt Island, Fla., under the trade name TUA Systems.

The elongated body 110 may have any suitable cross-sectional shape, including elliptical, polygonal, or prismatic, although a circular cross-section generally is preferred. The cross-sectional dimension generally is between about 0.01 millimeters to about 1.0 millimeters, preferably between about 0.10 millimeters and about 0.50 millimeters, most preferably between about 0.250 millimeters and about 0.450 millimeters. Furthermore the guidewire 100 may have an overall length between about 180 centimeters and 400 centimeters, preferably between about 250 centimeters and about 350 centimeters, more preferably the medical device has a length between about 290 centimeters and about 310 centimeters, and most preferably about 300 centimeters.

Referring now to FIG. 2 there is shown a partial cross-sectional side view of the distal end portion of the guidewire 100. As shown in FIG. 2, a flexible tip 160 may extend from the distal end portion of the elongated body 110. A variety of distal tip configurations are known and used in the art, each generally capable of performing particular functions. For example, and as embodied herein, the flexible tip 160 is constructed of a solid inner core wire 162 of type 304 stainless steel, wherein the solid core 162 is wrapped with a bio-compatible wire 164. Examples of a bio-compatible wire 14 which maybe utilized include stainless steel, Nitinol, titanium, platinum, iridium, and similar bio-compatible materials. In a preferred embodiment the bio-compatible wire 164 is a platinum wire. Platinum wire is preferably used because platinum wire is visible under fluoroscopy thereby enabling a surgeon to locate the flexible tip 160 within a patient's body in use. The guidewire 100 includes a pre-formed curve 169, in addition to a blunt tip 167 form, includes an atraumatic tip thereby allowing the guidewire 100 to be inserted within a patient's vasculature. The pre-formed curve 169 ensures that the blunt tip 167 does not pierce the vessel/artery or organ through which the guidewire 100 is being advanced. It shall be understood that the pre-formed curve 169 remains sufficiently pliable and elastic whereby an interventional device may be advanced over the outer diameter of the guidewire 100 such that the pre-formed curve 169 will straighten and allow the medical device to pass over. Such tip designs are well-known in the art.

As previously noted, an inflatable balloon 120 is provided at the distal end portion of the guidewire 100 of the present invention. The balloon 120 may be constructed of any suitable, flexible bio-compatible materials depending upon the intended function of the guidewire 100. The balloon 120 may be inelastic, if desired, although generally elastic materials are preferred. Examples of materials of which the balloon 120 may be formed are urethane, pebax, polyvinyl chloride, silicone or other similar materials which have good elastomeric properties. The balloon 120 may be constructed of C-Flex, which is available from Consolidated Polymer Technologies, Inc. of Largo, Fla., USA. The C-Flex material allows for the formation of a balloon having very specific durometers, thereby enabling the balloon to be specifically tuned to be responsive to a pre-determined force. For example, if a pressure of one atmosphere or about 14 psi is available to be applied to a balloon and it is desirable to inflate the balloon from a first diameter of 0.90 millimeters to a second diameter of about 6 millimeters, the durometer of the C-Flex may be adjusted thereby allowing for a balloon to be formed which will expand from the first diameter to the second desired diameter in response to the applied force.

As embodied herein, specifically with reference to FIGS. 1 and 2, the balloon 120 may be radially disposed at the distal end portion of the elongated body 110, wherein the balloon 120 is in fluid communication with the lumen 101 of the elongated body 110 through at least one aperture 107 formed within the wall of the elongated body 110. The aperture 107 may be formed having a generally cylindrical geometry or the aperture may be formed as an elongated slit within the wall of the elongated body 110. Furthermore, it is contemplated that the aperture 107 may be embodied having many different geometric shapes and the examples above and those which are shown in the figures are merely exemplary.

Alternatively, the balloon 120 may be disposed asymmetrically upon only a portion of the outer wall circumference if desired. Furthermore, if desired, the proximal end of the balloon 120 may be disposed about the extreme distal end of the elongated body 110 as depicted by U.S. Pat. No. 5,807,330, to George P. Teitelbaum, entitled "Angioplasty Catheter," the entirety of which is hereby incorporated by reference.

As previously noted, and in accordance with the present invention the guidewire 100 also includes a valve body 150 configured to be moveably disposed at the proximal end portion of the elongated body 110. The valve body 150 is movable between a closed position and an open position, wherein the valve body is configured to engage a surface of the elongated body, to seal the opening when the valve body is in the closed position.

The valve body 150 may be configured to be movable in either an axial or radial direction. In a preferred embodiment, the valve body 150 can be moved axially between a sealed position and an opened position, and moved radially to engage or disengage a locking mechanism disposed upon the proximal end portion of the medical device.

The valve body 150 when in a closed position is preferably flush with the outer diameter of the elongated body 110 as shown in FIG. 4. By providing such a low profile valve body, interventional devices may be easily passed over the guidewire 100. In an alternative embodiment, it is contemplated that the valve body 150 may have a diameter greater than that of the elongated body 110, so long as the outer diameter of the valve body 150 is not so large as to inhibit the passage of interventional devices thereover.

Referring now to FIG. 3, there is shown a preferred embodiment of the valve body 150 in accordance with one aspect of the present invention. The valve body 150 includes a proximal end portion 154 and a distal end portion 152, and a cavity or/lumen 151 formed there between. The distal end portion 152 of the valve body is adapted to sealingly engage the outer diameter of the elongated body as shown in FIG. 4.

The cavity 151 of the valve body 150 may further include a pliable coating to aid in the sealing of the valve body to the elongated body 110. The coating may be silicone, urethane, or TFE. In a preferred embodiment the pliable coating is a parylene coating.

The valve body may be constructed of any suitable bio-compatible material such as titanium, Nitinol, polymide, and other bio-compatible plastics. In a preferred embodiment the valve body is constructed of a stainless steel tube, wherein the proximal end 154 of the tube is sealed with a plug 158. The plug 158 may be constructed of a bio-compatible material such as titanium, Nitinol, stainless steel, nylon, delrin, and other similar materials. It is further contemplated that the valve body may be constructed of a unitary body wherein the valve body may be injection molded and being constructed of plastics or metals.

Referring now to FIGS. 3 and 4 there is shown the valve body of the medical device 10 in accordance with one aspect of the present invention in use. As shown in FIG. 4, the valve body 150 is disposed upon the proximal end portion of the elongated body 110, wherein the valve body is in a closed position. The distal end 152 of the valve body forms a fluid tight seal with the step 117 of the elongated body 110. The fluid tight seal may be formed through an interference fit between the distal tip 152 of the valve body and the step 117 or alternatively, as described herein the inner diameter of the valve body may include a parylene coating for enhanced sealing properties. Referring now to FIG. 3 there is shown the valve body 150 in an open configuration. Wherein, when the valve body 150 is in an open configuration having been moved a distance away from the step 117 as denoted by the reference number 90, inflation fluid may be introduced into the lumen 101 of the elongated body 110 thereby inflating the balloon 120 of the distal tip portion. Inflation fluid may be introduced in a manner such as that disclosed by Teitlebaum, U.S. Pat. No. 5,807,330. Alternatively, inflation fluid may be withdrawn from the lumen 101, thereby deflating the balloon 120. As shown in FIGS. 3 and 4, the valve body 150 may be selectively opened and closed in order to control the inflation and deflation of the balloon 120. To move the valve body between an opened and closed position as shown an axial force or a radial force or a combination thereof may be applied to either or both the valve body 150 or the elongated body 110. Additionally, the valve body 150 only need be moved between about 0.005 inches and about 1.0 inches, preferably between about 0.02 inches and about 0.75 inches, most preferably between about 0.05 inches and about 0.25 inches.

Although the present invention has been described above utilizing an inflatable member mounted upon the guidewire 100, it shall be understood that other structures can be utilized to achieve the same results. For example, it is contemplated that the inflatable member may be replaced by a structure having a membrane disposed thereabout, wherein the structure can comprise a plurality of slits formed in the guidewire, the distal end of the slits being coupled to an actuator mechanism such as a pull wire or the like. A flexible membrane is disposed over the plurality of slits, wherein upon applying a force to the actuator the plurality of slits expand from the surface of the guidewire thereby impeding flow within the lumen. Such a device is shown and disclosed in U.S. Pat. Application Publication No. 2007/0021685 entitled "Guidewire Apparatus With An Expandable Portion and Methods of Use", the entirety of which is hereby incorporated by reference.

Figure 13:
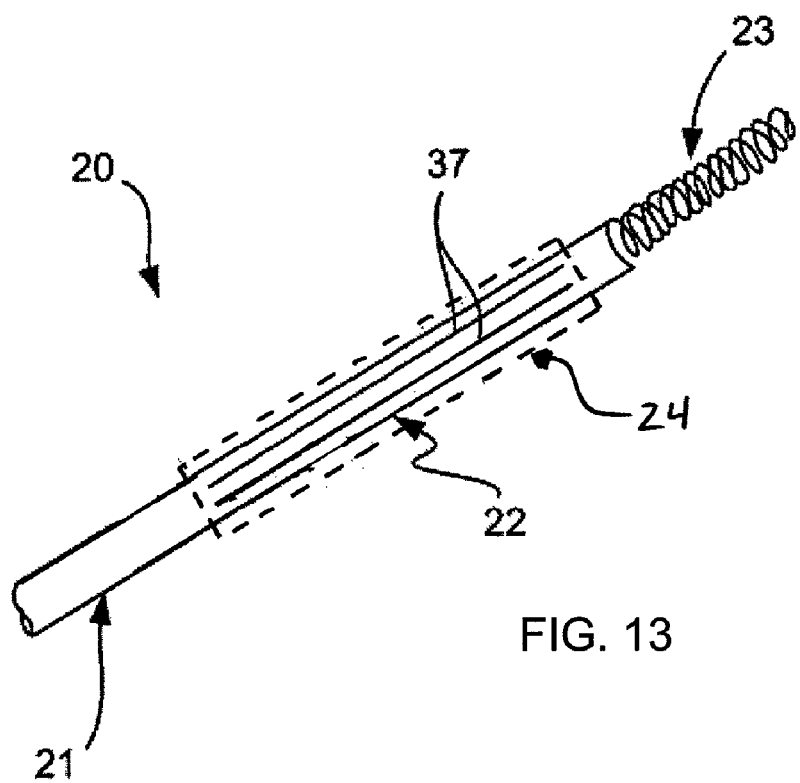
FIGS. 13 and 14 illustrate an embodiment of the occlusion device in an unexpanded, undeployed position (FIG. 13) and an expanded, deployed position (FIG. 14).
Figure 14:
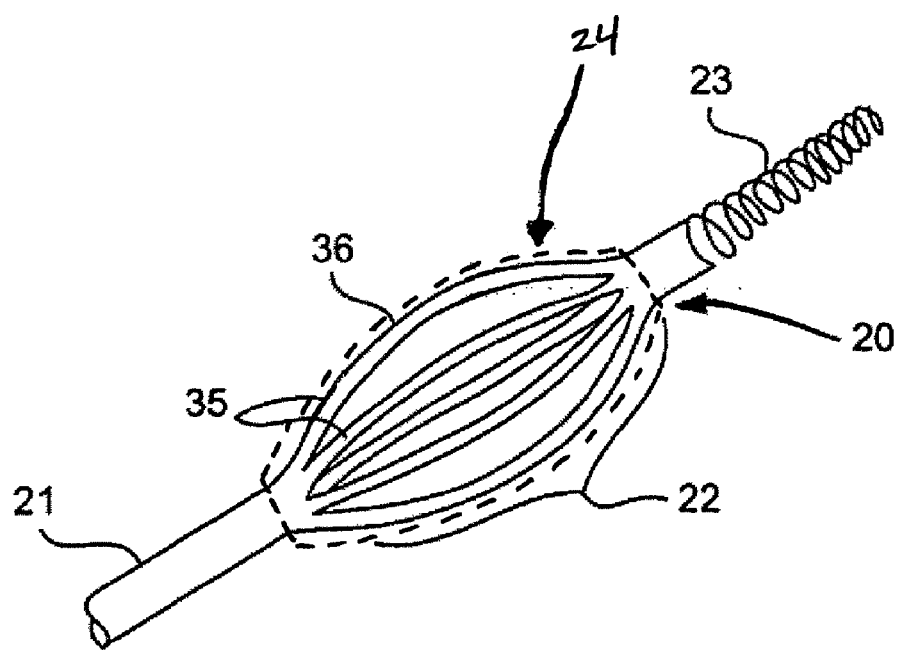

For example, FIGS. 13 and 14 show medical device 20 comprising body 21, expandable section 22 and distal end 23. The device comprises expansion elements 35 defined by a plurality of substantially parallel elongated slits 37, each of which is disposed radially about, and extends substantially parallel to, the longitudinal axis of the expandable section 22. These slits 37 may be cut or formed directly into body 21 utilizing known manufacturing processes. The slits are shown in an unexpanded, first undeployed position in FIG. 13 and an expanded, second deployed position in FIG. 14. A flexible membrane shown by dotted line 24 is disposed over the plurality of slits. Each expansion element 35 resiliently bows radially outward such that the collective elements expand substantially transversely with respect to the longitudinal axis from the unexpanded state and the expanded state. As each expansion element 35 is urged toward the expanded state, a respective apex portion 36 of each element may be applied to contact a selected surface to secure membrane 24 against a wall of the vessel thereby impeding flow within the lumen.

Figure 5:
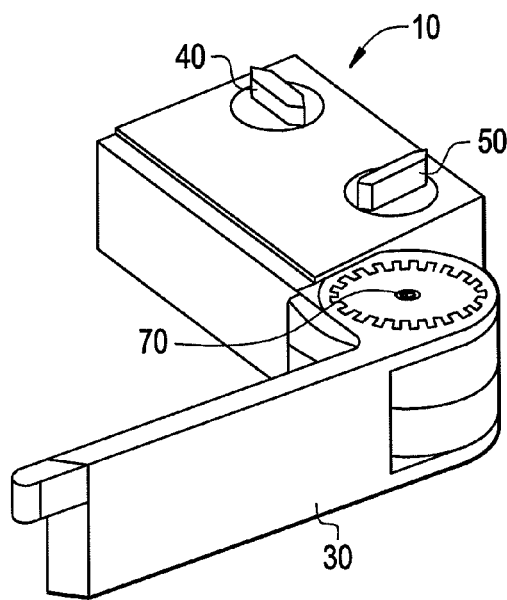
FIG. 5 is an isometric view of an inflation device to be utilized with the catheter of FIG. 1.

Referring now to FIG. 5, there is shown an inflation device 10 that can be utilized in combination with the guidewire 100 as described above. The inflation device 10 includes a chamber 70 in which the proximal end of the guidewire 100 is received. Upon closing a lever 30 of the inflation device, the valve body 150 is opened, thereby allowing fluid to be injected into the lumen 101 of the guidewire 100 by rotating one of the knobs 40 or 50 to inflate the balloon 120. The lever 30 can then be opened, thereby closing the valve body 150, while retaining the balloon 120 in an inflated configuration. The above procedure can be performed multiple times to inflate/deflate the balloon 120 of the guidewire 100. Further description of a suitable inflation device that may be utilized with the guidewire 100 as described herein is shown and described in U.S. Pat. Application Publication No. 2003/001407, the entirety of which is hereby incorporated by reference.

Figure 6:
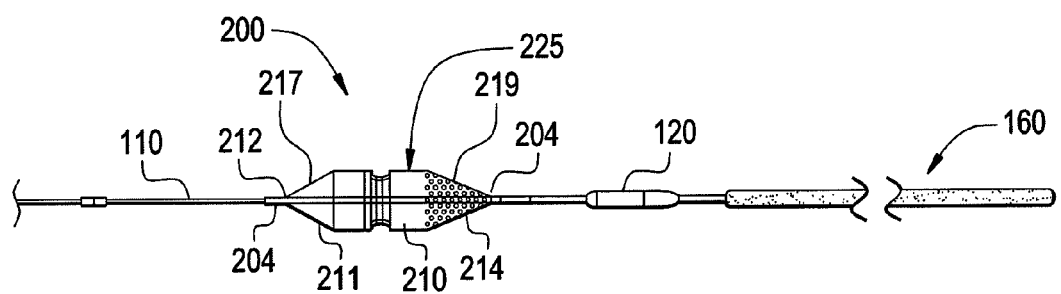
FIG. 6 is a plan view of an embolic protection filter to be utilized with the present invention.

Referring now to FIG. 6, there is shown an exemplary embodiment of an embolic protection filter 225 that may be utilized in accordance with the methods of the present invention. The filter includes a frame member having a proximal end and a distal end and a membrane disposed on a portion of the frame. The frame being movable between a collapsed position and an expanded position. The frame is slidably disposed over a member such as the elongated body as described herein.

Referring to FIG. 6 there is illustrated an embolic protection device according to the invention indicated generally by the reference number 200. The device 200 is configured to be disposed over the guidewire 100 as described above. At least one tubular sleeve 204 is configured to slidably receive the elongated member 110, wherein the at least a portion of the filter 225 is mounted to the sleeve 204, the filter 225 being movable between a collapsed stored position against the sleeve 204 and an expanded position as shown in the drawings extended outwardly of the sleeve 204 for deployment in a blood vessel.

The filter 200 comprises a mesh net 210 mounted over a collapsible support frame 211. The mesh net 210 is gathered into the sleeve 204 at each end, the net 210 being rigidly attached to a proximal end 212 of the sleeve 204 and the net 210 being slidable along a distal end 214 of the sleeve 204. Thus the distal end of the net 210 is longitudinally slidable along the sleeve 204. The support frame 211 is also fixed at the proximal end 212 of the sleeve 204. A distal end (not shown) of the support frame 211 is not attached to the sleeve 204 and is thus also free to move longitudinally along the sleeve 204 to facilitate collapsing the support frame 211 against the sleeve 204. The support frame 211 is such that it is naturally expanded as shown in the drawings and can be collapsed inwardly against the sleeve 204 for loading in a catheter 218, shown in FIG. 8, or the like.

The filter 200 has large proximal inlet openings 217 and small distal outlet openings 219. The proximal inlet openings 217 allow blood and embolic material to enter the filter body, however, the distal outlet openings 219 allow through passage of blood but retain undesired embolic material within the filter body. Enlarged openings are provided at a proximal end of the filter net 210 to allow ingress of blood and embolic material into an interior of the net 210.

Figure 8:
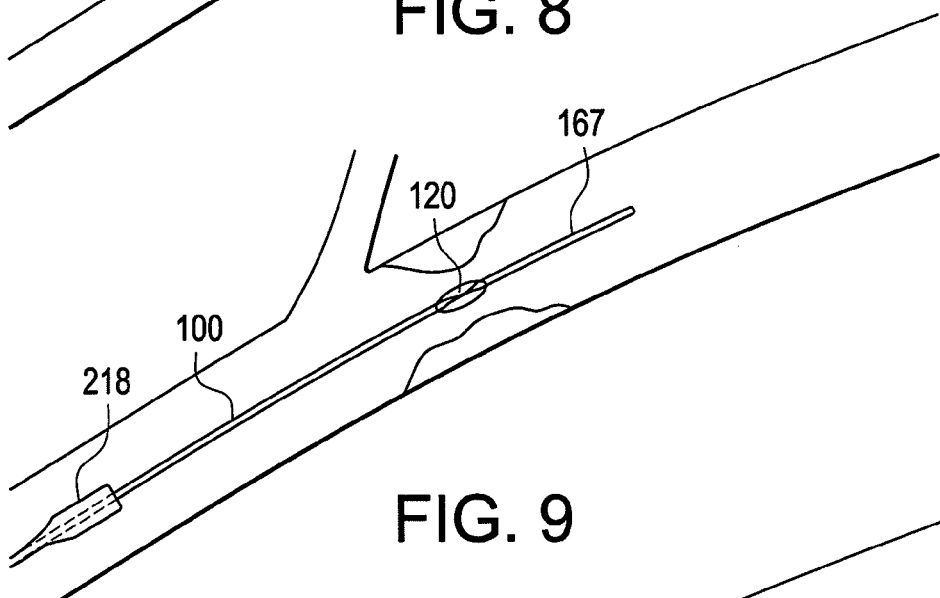
FIG. 8 is an exemplary embodiment of an artery including a stenosed area illustrating the catheter of FIG. 1 passing through the stenosed area.

In use, the filter 225 is mounted in a collapsed state within a distal end of the catheter 218, shown in FIG. 8, and delivered to a deployment site. When the filter is correctly positioned the catheter 218 is retracted allowing the support frame 211 to expand inflating the net 210 across the vessel in which the filter is mounted. Blood and emboli can enter the enlarged openings at a proximal end of the net 210. The blood will pass through the net wall, however, the openings or pores in the net are sized so as to retain the embolic material. After use the catheter is delivered along the guidewire 100 and slid over the filter 225 engaging the proximal inlet end 217 first to close the openings and then gradually collapsing the net against the sleeve 204 as the catheter 218 advances over the filter 225. Once the filter 225 is fully loaded in the catheter 218, it can then be withdrawn.

The catheter 218 engages the proximal end of the filter net first thus closing the filter net inlet and preventing escape of embolic material from the filter net as the filter net is being collapsed.

Conveniently the tip of the catheter 218 which forms a housing or pod for reception of the filter is of an elastic material which can radially expand to accommodate the filter with the captured embolic material. By correct choice of material, the same catheter or pod can be used to deploy and retrieve the filter. For deployment, the elastic material holds the filter in a tightly collapsed position to minimize the size of the catheter tip or pod. Then, when retrieving the filter 225, the catheter tip or pod is sufficiently elastic to accommodate the extra bulk of the filter due to the embolic material.

Also, the filter 225 is not fast on the guidewire 100 and thus accidental movement of the guidewire is accommodated without unintentionally moving the filter, for example, during exchange of medical devices or when changing catheters.

Conveniently also when the filter has been deployed 225 in a lumen such as a blood vessel or artery, the catheter can be removed leaving a bare guidewire 100 proximal to the filter for use with known devices such as balloon catheter and stent devices upstream of the filter.

Referring now to FIGS. 7 through 12 there is shown methods of use of the devices described above in accordance with the present invention.

Figure 7:
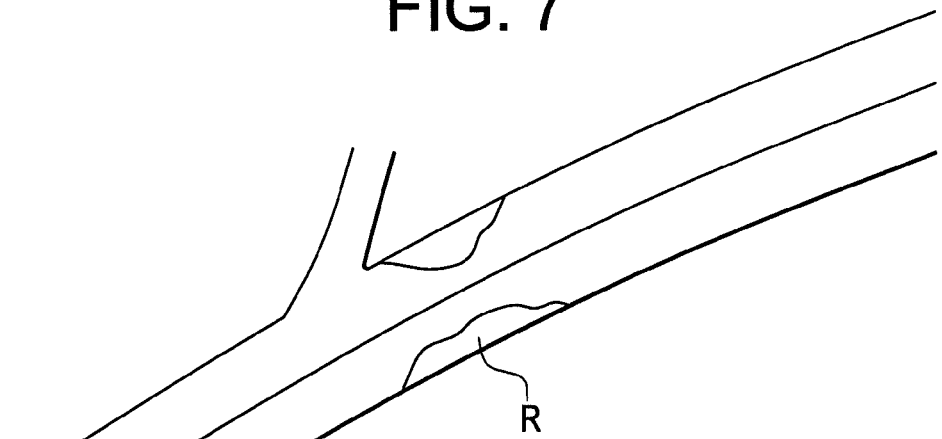
FIG. 7. is an exemplary embodiment of an artery illustrating a stenosed area.

As shown in FIG. 7, there is shown an exemplary embodiment of a lumen, such as the carotid artery, wherein there is shown a stenosed area R, the stenosed area may be plaque, calcified lesion or another type of obstruction within the lumen. The obstruction can range from minimally occluding the vessel to fully occluding the vessel. In the instance of carotid artery occlusions, it is desirable to pass an embolic protection device through the occlusion and deploy the device distal to the lesion, so that any particulate or emboli formed during subsequent procedures is captured by the embolic protection device or not allowed to flow distally to the patient's brain due to occlusion in the vessel.

Referring now to FIG. 8, there is shown the guidewire 100 in accordance with the present invention, wherein the guidewire 100 is being advanced distally through the lesion R, wherein the inflatable balloon 120 disposed on the distal end of the guidewire 100 is in an undeployed position. By passing the guidewire through the lesion first, this allows for a lower crossing profile through the lesion R, thereby lessening the chance of disturbing the lesion and forming emboli. Additionally, as shown in FIG. 8, the delivery catheter 218 is slidably disposed over the guidewire 100, wherein the delivery catheter 218 includes the filter 225 as described above.

Figure 9:
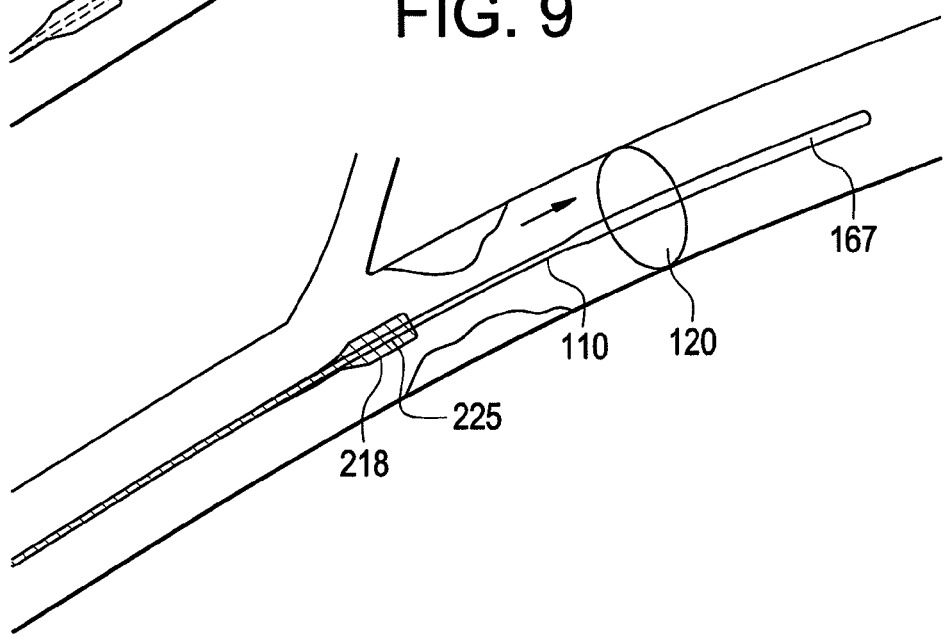
FIG. 9 is an exemplary embodiment of an artery including a stenosed area illustrating the catheter of FIG. 1 having been passed through the stenosed area and deployed to temporarily occlude a vessel.

Referring now to FIG. 9, the balloon 120 disposed on the guidewire 100 has been advanced distal to the lesion R, wherein the proximal end of the guidewire can then be disposed in the inflation device of FIG. 5, the valve body 150 moved to an open position to allow the user to inflate the balloon 120, thereby occluding the lumen and restricting flow distally D within the lumen. By restricting the flow in the lumen, any embolic material present in the lumen cannot pass distal to the occlusion device.

Figure 10:
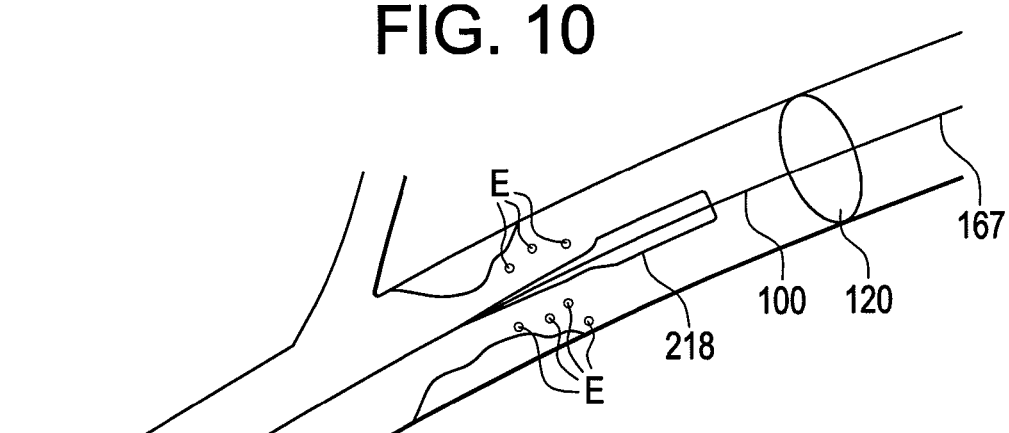
FIG. 10 illustrates the step of passing a deployment catheter containing an embolic protection filter past the stenosed area.
Figure 11:
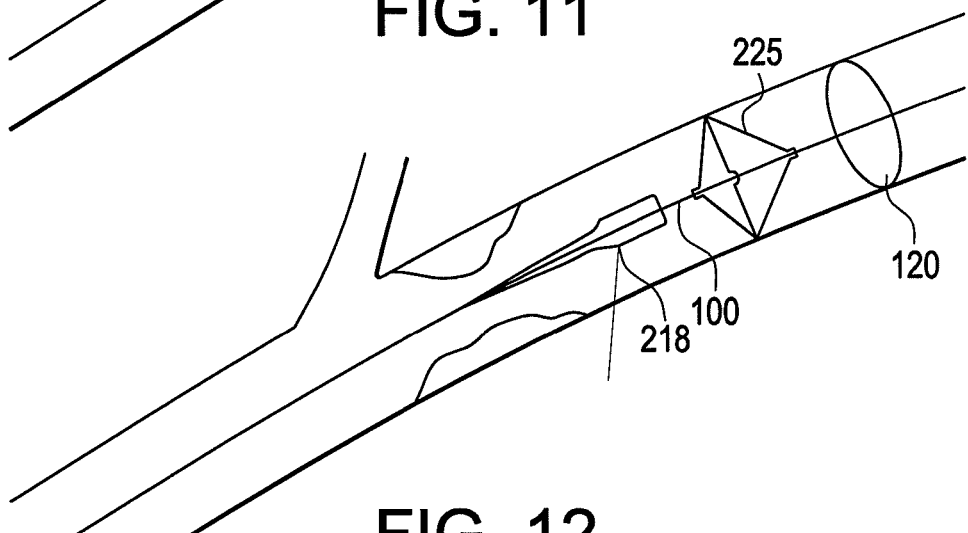
FIG. 11 illustrates deployment of the embolic protection filter between the stenosed area and the deployed occlusion device.

Referring now to FIG. 10, there is shown the delivery catheter 218 of the present invention, wherein the delivery catheter includes the filter 225 disposed therein in a collapsed delivery state. As shown in FIG. 10, the delivery catheter 218 and the Filter 225 are advanced distally through the lesion R. The embolic material E that is dislodged during the crossing of the lesion by the larger diameter delivery catheter 218 remains within the lumen suspended due to the restricted fluid flow in the vessel as described above. As shown in FIGS. 9-11, the balloon 120 of the guidewire 100 is deployed distal to the lesion but spaced sufficiently distal to the lesion R to allow for the filter 225 to be deployed proximal to the balloon 120 but distal to the lesion R. As shown in FIG. 11, the filter 225 is deployed within the lumen using the delivery catheter 218, wherein after deployment of the delivery catheter the delivery catheter 218 can be removed from the guidewire 100.

Figure 12:
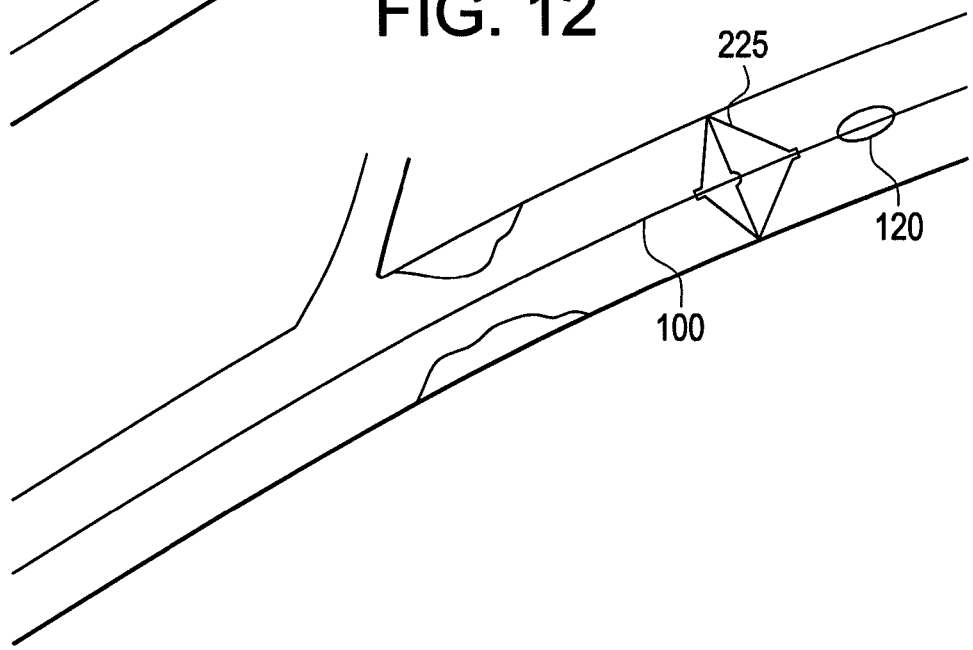
FIG. 12 illustrates retraction of the occlusion device to restore fluid flow within the lumen.

Referring now to FIG. 12, after deployment of the filter 225, the balloon 120 is then deflated to its undeployed state as shown. By deflating the balloon 120, fluid flow within the lumen is restored, wherein any embolic material dislodged during the crossing of the larger diameter delivery catheter/filter assembly is then captured by the filter 225. After fluid flow is restored a subsequent medical procedure may be performed within the lumen and lesion area R, examples of such procedures may be angioplasty, stenting, atherectomy or other suitable medical procedures for treating the lesion R.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

What is claimed is:

1. A method for reducing emboli formation, comprising:
providing a first medical device, the first medical device comprising an occlusion member associated with a distal end thereof;
advancing the first medical device through a stenosis of a vessel to an occluding position that is distal the stenosis;
activating the occlusion member of the first medical device at the occluding position to restrict fluid flow across the stenosis;
providing an embolic protection filter having a collapsed state and an expanded state, the embolic protection filter comprising a polymeric filter membrane, a support structure supporting the membrane in the expanded state and a tubular element connected to the support structure and having an aperture for disposing the filter over a delivery device, wherein the embolic protection filter comprises a proximal inlet opening and a plurality of distal outlet openings, the outlet openings configured to allow fluid to flow through the filter but retain embolic material within the filter and the inlet opening is larger than any of the outlet openings;
distally advancing the embolic protection filter through the stenosis, while the occlusion member is activated and fluid flow across the stenosis is restricted, to a filtering position that is distal of the stenosis but proximal of the occluding position;
deploying the embolic protection filter at the filtering position from the collapsed state to the expanded state; and
deactivating the occlusion member of the first medical device after deploying the filter.

2. The method of claim 1, wherein the first medical device further comprises a guidewire and the occlusion member is an inflatable balloon.

3. The method of claim 2, wherein the first medical device further comprises a valve assembly disposed at a proximal end of the guidewire, the valve assembly movable between an open position and a closed position.

4. The method of claim 2, wherein the inflatable balloon is positioned at the distal end of the guidewire, the guidewire is sized to receive the embolic protection filter over the guidewire, and the filter is translatable and rotatable about the guidewire.

5. The method of claim 1, wherein the first medical device further comprises a guidewire.

6. The method of claim 5, wherein the guidewire is sized to receive the embolic protection filter over the guidewire, and the filter is translatable and rotatable about the guidewire.

7. The method of claim 1, wherein the first medical device is sized to receive the embolic protection filter thereover.

8. The method of claim 1, wherein the occlusion member is an inflatable balloon.

9. The method of claim 1, wherein the occlusion member comprises a plurality of slits formed adjacent a distal end of the catheter, the slits movable between a first undeployed position and a second deployed position.

10. The method of claim 1, further comprising performing a medical procedure after deploying the embolic protection filter.

11. The method of claim 10, wherein the medical procedure is balloon angioplasty.

12. The method of claim 10, wherein the medical procedure is deploying a stent.

13. The method of claim 10, wherein the first medical device further comprises a guidewire, and accidental movement of the guidewire during exchange of a medical device during the medical procedure is accommodated without unintentionally moving the embolic protection filter.

14. The method of claim 13, wherein the embolic protection filter is received within a space at a distal end of a delivery catheter, in its collapsed state, when the filter is advanced to the filtering position, and the medical procedure is deploying a stent.

15. The method of claim 14, wherein the occlusion member is an inflatable balloon.

16. The method of claim 10, wherein the medical procedure comprises deploying a stent at the stenosed area, and
  the stent is deployed after the occlusion member is deactivated and fluid flow across the stenosed area is restored.

17. The method of claim 1, wherein after activating the occluding member, any embolic material from the stenosis that is present in the vessel cannot pass distal to the occlusion member.

18. The method of claim 1, wherein the embolic protection filter is received within a space at a distal end of a delivery catheter, in its collapsed state, when the filter is advanced to the filtering position.

19. The method of claim 1, wherein fluid flow across the stenosis is restored by deactivating the occlusion member.

* * * * *